(12) United States Patent
Palmerton et al.

(10) Patent No.: US 8,608,816 B2
(45) Date of Patent: Dec. 17, 2013

(54) FLUID FILTRATION DEVICE AND SYSTEM

(75) Inventors: Christopher A. Palmerton, Williamsville, NY (US); Anthony Lizauckas, III, Williamsville, NY (US); Gregory Pepe, Lancaster, NY (US); Daniel R. Palmerton, Elma, NY (US); Samantha Bonano, Williamsville, NY (US); Kyrylo Shvetsov, Tonawanda, NY (US)

(73) Assignee: Buffalo Filter LLC, Lancaster, NY (US)

(*) Notice: Subject to any disclaimer, the term of this patent is extended or adjusted under 35 U.S.C. 154(b) by 0 days.

(21) Appl. No.: 13/476,041

(22) Filed: May 21, 2012

(65) Prior Publication Data

US 2013/0174525 A1 Jul. 11, 2013

Related U.S. Application Data

(60) Provisional application No. 61/584,897, filed on Jan. 10, 2012.

(51) Int. Cl.
*B01D 46/00* (2006.01)

(52) U.S. Cl.
USPC .............. 55/319; 55/385.1; 604/35; 604/319; 604/902; 606/39

(58) Field of Classification Search
USPC ........ 55/385.1, 392, 394, 429, 466, 337, 413, 55/418, 458, 459.1, 462, 463, 331, 336, 55/414, 416, 315, 319, 320; 95/273, 286; 96/4, 396, 413, 417; 600/532, 543; 604/33, 45, 264; 606/40; 128/205.12; 73/863.23
See application file for complete search history.

(56) References Cited

U.S. PATENT DOCUMENTS

| | | | |
|---|---|---|---|
| 3,596,441 | A | 8/1971 | Lundahl |
| 3,736,728 | A | 6/1973 | Kleissler, Jr. |
| 3,858,572 | A | 1/1975 | Binard |
| 3,903,727 | A | 9/1975 | Sweet |
| 4,048,992 | A | 9/1977 | Lindemann |

(Continued)

FOREIGN PATENT DOCUMENTS

| | | |
|---|---|---|
| EP | 2305157 A1 | 4/2011 |
| WO | WO2009/111259 A1 | 9/2009 |

OTHER PUBLICATIONS

Ball, Controlling Smoke Evacuation and Odor During Laser Surgery, Today's OR Nurse, vol. 8, No. 12, Dec. 1986.

(Continued)

*Primary Examiner* — Duane Smith
*Assistant Examiner* — Minh-Chau Pham
(74) *Attorney, Agent, or Firm* — Phillips Lytle LLP

(57) ABSTRACT

A medical fluid filter system is provided having a housing having: a liquid trap chamber having a volume; a filter media chamber; a filter media arranged within the filter media chamber; the liquid trap chamber having a liquid trap outlet port in fluid communication with the filter media chamber; the liquid trap outlet port configured and arranged within the liquid trap chamber to inhibit flow of liquid from the liquid trap chamber to the filter media chamber and configured and arranged to allow gas to flow from the liquid trap chamber to the filter media chamber; a filter system inlet passing through the housing for intake of fluid originating from a surgical site; and a filter system outlet passing through the housing for fluid exhaust.

20 Claims, 12 Drawing Sheets

(56) References Cited

U.S. PATENT DOCUMENTS

| | | | |
|---|---|---|---|
| 4,106,213 A | 8/1978 | Witte | |
| 4,220,633 A | 9/1980 | Pirsh | |
| 4,270,725 A | 6/1981 | Scott | |
| 4,324,574 A | 4/1982 | Fagan | |
| 4,382,440 A | 5/1983 | Kapp | |
| 4,451,258 A | 5/1984 | Jensen | |
| 4,477,270 A | 10/1984 | Tauch | |
| 4,487,606 A | 12/1984 | Leviton | |
| 4,538,594 A | 9/1985 | Boebel | |
| 4,561,868 A | 12/1985 | von Reis | |
| 4,735,603 A | 4/1988 | Goodson | |
| 4,787,894 A | 11/1988 | Turnbull | |
| 4,813,931 A | 3/1989 | Hauze | |
| 4,874,513 A | 10/1989 | Chakraborty | |
| 4,906,261 A | 3/1990 | Mohajer | |
| 4,930,997 A | 6/1990 | Bennett | |
| 4,936,318 A | 6/1990 | Schoolman | |
| 4,957,492 A | 9/1990 | McVay | |
| 5,002,534 A | 3/1991 | Rosenblatt | |
| 5,047,010 A | 9/1991 | Amz | |
| 5,069,792 A | 12/1991 | Prince | |
| 5,098,375 A | 3/1992 | Baier | |
| 5,127,411 A | 7/1992 | Schoolman | |
| 5,246,419 A | 9/1993 | Absten | |
| 5,249,579 A | 10/1993 | Hobbs et al. | |
| 5,279,549 A * | 1/1994 | Ranford | 604/34 |
| 5,336,169 A | 8/1994 | Divilio | |
| 5,360,396 A | 11/1994 | Chan | |
| 5,417,655 A | 5/1995 | Divilio | |
| 5,451,222 A | 9/1995 | De Maagd | |
| 5,578,000 A | 11/1996 | Greff | |
| 5,688,256 A | 11/1997 | Surratt | |
| 5,709,675 A | 1/1998 | Williams | |
| 5,722,962 A | 3/1998 | Garcia | |
| 5,824,138 A | 10/1998 | Taylor, III | |
| 5,897,525 A | 4/1999 | Dey | |
| 6,110,259 A | 8/2000 | Schultz | |
| 6,203,590 B1 * | 3/2001 | Byrd et al. | 55/319 |
| 6,544,210 B1 | 4/2003 | Trudel | |
| 6,576,033 B1 | 6/2003 | Booth | |
| 6,585,791 B1 * | 7/2003 | Garito et al. | 55/385.1 |
| 6,589,316 B1 | 7/2003 | Schultz | |
| 6,592,543 B1 | 7/2003 | Wortrich | |
| 6,746,504 B2 | 6/2004 | Booth | |
| 6,881,236 B2 | 4/2005 | Schultz | |
| 7,258,712 B2 | 8/2007 | Schultz | |
| 7,402,197 B2 * | 7/2008 | Larsen et al. | 96/4 |
| 7,789,946 B2 | 9/2010 | Schultz | |
| 7,819,954 B2 * | 10/2010 | Larsen et al. | 96/4 |
| 7,819,957 B2 * | 10/2010 | Roberts et al. | 96/132 |
| 7,959,698 B2 | 6/2011 | Schultz | |
| 8,114,181 B2 * | 2/2012 | Gogolin | 55/385.1 |
| 2002/0128603 A1 * | 9/2002 | Booth et al. | 604/164.01 |
| 2004/0128962 A1 * | 7/2004 | Jeanfreau | 55/385.1 |
| 2005/0022810 A1 * | 2/2005 | Moore et al. | 128/202.26 |
| 2007/0137484 A1 * | 6/2007 | Roberts | 95/273 |
| 2007/0249990 A1 | 10/2007 | Cosmescu | |
| 2009/0101562 A1 * | 4/2009 | Newton | 210/232 |
| 2009/0221963 A1 | 9/2009 | Lloyd | |
| 2010/0094200 A1 | 4/2010 | Dean | |

OTHER PUBLICATIONS

Descoteaux, Preliminary study of electrocautery smoke particles produced in vitro and during laparoscopic procedures, Surgical Endoscopy, vol. 10, 1996, p. 152-158.

Pall Medical Brochure, Gas Filtration Products for OEM Health Care Devices, 2003, Pall Corporation.

* cited by examiner

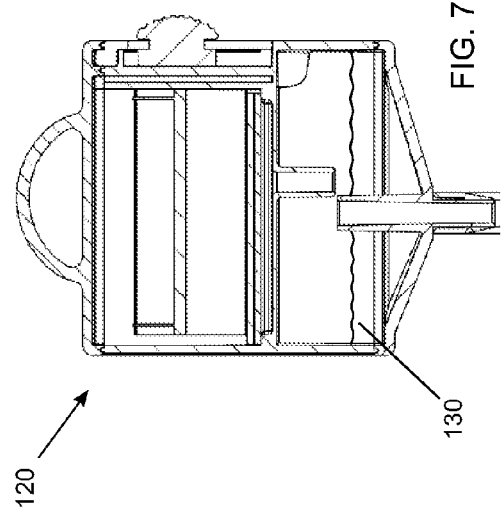
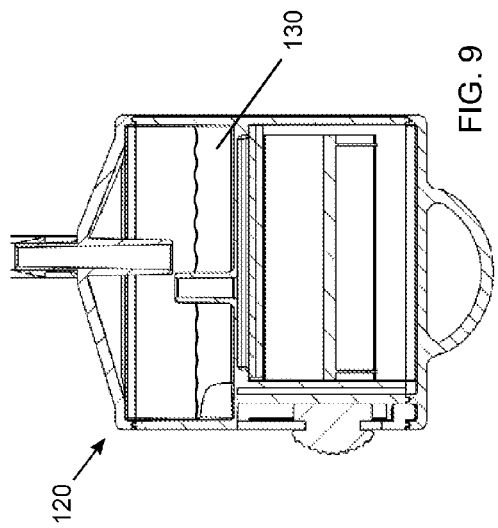
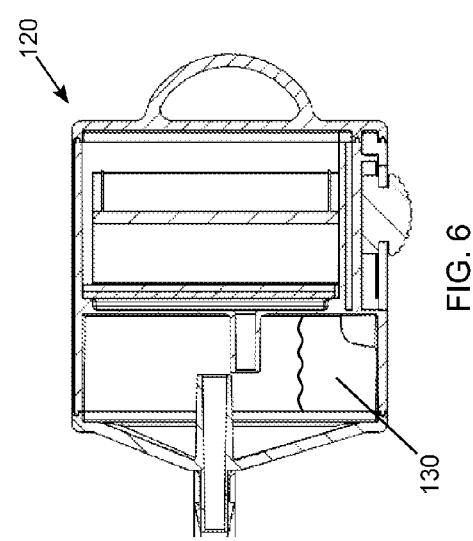
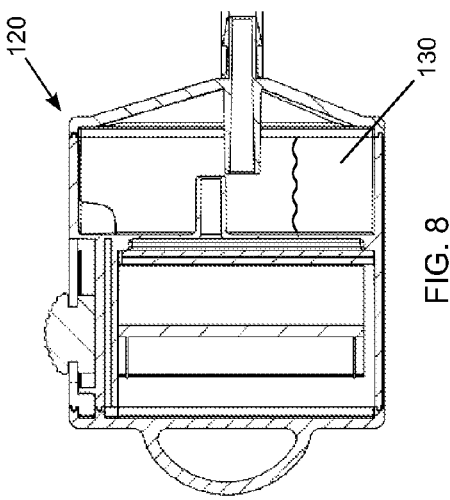

FLUID FILTRATION DEVICE AND SYSTEM

BACKGROUND OF THE INVENTION

The present application claims the benefit of U.S. Provisional Application No. 61/584,897, filed Jan. 10, 2012; which is hereby incorporated by reference in its entirety.

BACKGROUND OF THE INVENTION

The present invention relates generally to fluid filtration and more specifically to methods and devices for fluid filtration in a medical environment.

BRIEF SUMMARY OF THE INVENTION

With reference to the corresponding parts portions or surfaces of the disclosed embodiment, merely for the purposes of illustration and not by way of limitation, provided is a medical fluid filter system (100) comprising a housing (120) comprising: a liquid trap chamber (128) having a volume; a filter media chamber (138); a filter media (143) arranged within the filter media chamber; the liquid trap chamber having a liquid trap outlet port (131) in fluid communication with the filter media chamber; the liquid trap outlet port configured and arranged within the liquid trap chamber to inhibit flow of liquid from the liquid trap chamber to the filter media chamber and configured and arranged to allow gas to flow from the liquid trap chamber to the filter media chamber; a filter system inlet (117) passing through the housing for intake of fluid originating from a surgical site; and a filter system outlet (134) passing through the housing for fluid exhaust.

The liquid trap outlet port may be generally near the center of volume of the liquid trap chamber.

The liquid trap outlet port may be above a lowest position within the liquid trap chamber for any orientation of the system in a gravitational field.

The liquid trap outlet port may be arranged in a position separated from an inner surface of the liquid trap chamber towards a generally central region of the liquid trap chamber.

The liquid trap chamber may have an inlet port in communication with the system inlet configured and arranged within the liquid trap chamber to inhibit flow of liquid from the liquid trap chamber out of the inlet port.

The liquid trap chamber may have an inlet port in fluid communication with the system inlet and configured and arranged within the liquid trap chamber to inhibit flow of liquid from the liquid trap chamber out of the inlet port and the fluid trap inlet port may be generally near the center of volume of the liquid trap chamber.

The filter media may be configured and arranged to filter surgical smoke.

The medical fluid filter system may further comprise a sliding valve (133).

The medical fluid filter system may further comprise a blower (370).

The system may be configured and arranged to use an inertial force caused by a circular flow path to separate liquid from the fluid.

In another aspect, a medical fluid filter system (100) is provided comprising: a filter system inlet (117) for intake of fluid originating from a surgical site; a housing (120) in fluid communication with the filter system inlet, the housing having: a filter media chamber (138) for receiving a filter media (143); a liquid trap chamber (128) for retaining liquids from the fluid and the liquid trap chamber having a volume; a generally tubular liquid trap outlet (131) extending into the volume and in fluid communication with the filter media chamber; a filter system outlet (134) passing through the housing for fluid exhaust.

The liquid trap outlet has an end located generally near the center of volume of the liquid trap chamber.

The liquid trap outlet port and the fluid trap inlet port may share a common wall.

The liquid trap chamber and the filter media chamber share a common wall.

The system may further have a filter media (143) configured and arranged to filter surgical smoke.

The system may further contain a moisture indicator (321) for indicating when the filter media is wet.

The liquid trap chamber may contain an inner peripheral surface for containing a liquid in at least two orientations of the medical fluid filter system.

The system may further contain a sliding valve (133).

The system may further contain a blower (370).

The system may be configured and arranged to use an inertial force caused by a circular flow path to separate liquid from the fluid.

In another aspect, a liquid trap system (120) is provided comprising: a system inlet (123); a system outlet (134); a hollow liquid trap chamber (128) having: an outer boundary (129), a liquid trap chamber inlet (151) in fluid communication with said system inlet, and a liquid trap chamber outlet (131) in fluid communication with said system outlet; said liquid trap chamber outlet arranged in a position separated a distance from said outer boundary towards a generally central region (150) of said liquid trap chamber.

The liquid trap system may further have a filter media chamber arranged between the liquid trap chamber outlet and the system outlet and may have a filter media arranged within the filter media chamber. The filter media may be pleated and may be configured and arranged to filter surgical smoke.

The liquid trap system may further have a valve. The valve may be a sliding valve.

The liquid trap system may further have a moisture wick, a liquid capturing gel, an attachment clip, and/or an attachment loop. The liquid trap chamber may be transparent. The filter media may have an antimicrobial substance.

The liquid trap system may further have a pump, a blower, and/or an impeller. The liquid trap system may further have a liquid exit port and may have a a container for storage of liquid from the liquid exit port. The liquid trap system may further have a moisture indicator for indicating when the filter media may be wet.

The liquid trap chamber may be in a generally cylindrical shape or a generally rectangular prism shape, for example. The liquid trap system may further have an obstruction between the system inlet and the system outlet. The liquid trap system may further have a hydrophobic media arranged across the fluid trap outlet.

The system may be configured and arranged to use a centrifugal force caused by a fluid flow to separate liquid from the fluid.

The liquid trap system may further have a biodegradeable material. The system may be sterile.

The system may be configured for connection to a wall suction unit. The liquid trap system may further have a power source. The power source may be a battery.

In another aspect, provided is a fluid filter system (100) having: a housing (120); a filter system inlet (117); a filter system outlet (134); a liquid trap chamber (128) having an outer boundary (129) and a liquid trap inlet (151) in fluid communication with the system inlet (117); the liquid trap outlet (131) arranged in a generally central region of the liquid trap chamber (150); a filter media chamber (138) in fluid communication with the liquid trap outlet; a filter media (143) arranged within the filter media chamber; and the filter media chamber having an outlet (136) in fluid communication with the filter system outlet.

The liquid trap chamber outlet may be above a lowest position within the liquid trap chamber for any orientation of the system in a gravitational field. In addition, the liquid trap chamber inlet may be arranged in a position separated from the outer boundary towards a generally central region of the liquid trap chamber. The liquid trap chamber outlet may be arranged in a position which may be not in a direct flow path out of the liquid trap chamber inlet into the liquid trap chamber.

The filter media may be pleated and/or may be configured and arranged to filter surgical smoke. The filter system may further have a valve. The valve may be a sliding valve. The filter system may further have a moisture wick, a liquid capturing gel, an attachment clip, an attachment loop. The liquid trap chamber may be transparent. The filter media may have an antimicrobial substance.

The filter system may further have a pump, a blower, an impeller. The filter system may further have a liquid exit port and may have a container for storage of liquid from the liquid exit port.

The filter system may further have a moisture indicator for indicating when the filter media may be wet.

The housing may be in a generally cylindrical shape or a generally rectangular prism shape. The filter system may further have an obstruction between the system inlet and the system outlet. The filter system may further have a hydrophobic media arranged across the fluid trap outlet.

The system may be configured and arranged to use a centrifugal force caused by a fluid flow to separate liquid from the fluid.

The filter system may further have a biodegradeable material The system may be sterile. The system may be configured for connection to a wall suction unit. The filter system may further have a power source. The power source may be a battery.

The filter medias may have a first portion and a second portion. One of the filter portions may be pleated to maximize surface area, and/or may be configured as a sleeve. One of the filter portions may be odor reducing, harmful gas/substance adsorbing/absorbing/detoxifying, antimicrobial, hydrophilic, hydrophobic, and/or optimized to prevent passage of smoke. One of the filter portions may be activated carbon, and/or made of fibers. One of the filter portions may be a ULPA filter. A filter media cap may be provided to interface with one or more of the filter media portions.

The filter system input may include a tube. The tube may be made of clear material and may be configured to aid in viewing inside the tube to see flow blockages. The tube may be flexible and may be configured to block fluid flow when pinched with a clamp valve. The input may contain an input adapter and the input adapter may be a Luer-Lock adapter and/or may contain friction ridges, or screw threads. The input may contain a housing connection adapter and the housing connection adapter may also be a Luer-Lock adapter and/or may contain friction ridges, or screw threads.

The input may include an internal wick for absorbing or blocking liquid or moisture. The wick may contain a hydrophobic material or a liquid retaining material such as sodium polyacrylate. The wick may be configured and arranged to partially or substantially obstruct fluid flow in order to prevent a large pressure drop across the filter system for a given flow rate. The wick may be optimized to prevent the passage of materials which may damage the filter media.

The filter system may contain valve. The valve may be a sliding valve, a roller valve, a pinch valve, or a rotary valve. The sliding valve may contain friction ridges to aid in user ergonomics. The valve may be adapted to maintain peritoneal distention when the filter system is used in laparoscopic surgery. The valve may contain indicia for indicating when the valve is open, closed, or positioned at some quantitative level.

The liquid trap input and output may be arranged such that flow of liquid out of the input and into the chamber will not directly be in line with the liquid trap output. The direction of flow from the liquid trap input into the chamber may be directed to flow directly into a wall of the liquid trap chamber. The liquid trap may be configured and arranged to partially or substantially obstruct fluid flow and/or to prevent a large pressure drop across the filter system for a given flow rate.

The filter system housing may have an output adapter configured for attachment to a tube. The output adapter may be a Luer-Lock adapter and/or may contain friction ridges, or screw threads.

The attachment clip may contain an elastic member, friction ridges, and/or may be configured and arranged for attachment to a drape.

The attachment loop may be configured and arranged to be clamped or attached to a carabiner. The attachment loop may be a carabiner, or contain Velcro (hook and loop) straps.

The housing and/or other filter system components may be made of a special material that is light weight, strong, antimicrobial, biodegradable, or radiation proof. The material may be a plastic, polymer, polyethylene, lead, or other similar material. The material may be clear in order to view whether the liquid trap is filled with fluid or whether flow is blocked.

The housing may be welded together in order to make connections air tight. The housing and other filter system components may be ultrasonically welded.

The filter system may be configured and optimized for having its input connected to a high pressure surgical chamber and/or its output releasing to ambient air. The output may be configured and optimized to be connected to a suction unit or standard medical wall suction. The filter system may contain a balloon or bag for capturing the fluid that passes through the filter system.

The filter system may contain an RFID tag. The filter system may include an electronic data storage containing filter information. The filter system may contain an indicator for indicating a usage level of the filter system. The indicator may react through atmospheric exposure.

The filter system may contain a one way valve, and/or the one way valve may be configured and optimized to prevent material captured by the filter media from exiting the filter system input. The filter system may contain pressure valves at each of its ports to prevent contents from exiting the filter system unless a nontrivial pressure is applied across each valve. The valves may be configured to not allow any fluid flow through the system, even if the system is connected to a pressurized surgical site, unless a pressure differential from a suction unit is provided. The filter system may be configured and optimized for continuous use during a surgical procedure.

The filter system may contain a powered suction unit. The powered suction unit may be configured to provide a substantial or all of the pressure differential for driving fluid through the filter system. The fluid flow rate through the filter system may be about 3 liters per minute.

In addition the filter system may contain an RF transponder for communication with a trocar, a insufflator, or smartboom. The filter system may further contain one or more one way valves and the valves may be placed at the liquid trap chamber inlet and/or outlet, the filter chamber inlet and/or outlet, and/or the filter system inlet and/or outlet. The valves may also be automatic valves or electronic valves. The valves may also be biased to be normally closed to prevent any fluid in the filter system from exiting the system when the flow drive is off.

BRIEF DESCRIPTION OF THE DRAWINGS

FIG. 6 is a section view of the fluid filter system shown in FIG. 1 being used in a first orientation.

FIG. 7 is a section view of the fluid filter system shown in FIG. 1 being used in a second orientation.

FIG. 8 is a section view of the fluid filter system shown in FIG. 1 being used in a third orientation.

FIG. 9 is a section view of the fluid filter system shown in FIG. 1 being used in a fourth orientation.

DETAILED DESCRIPTION OF THE INVENTION

Figure 1:
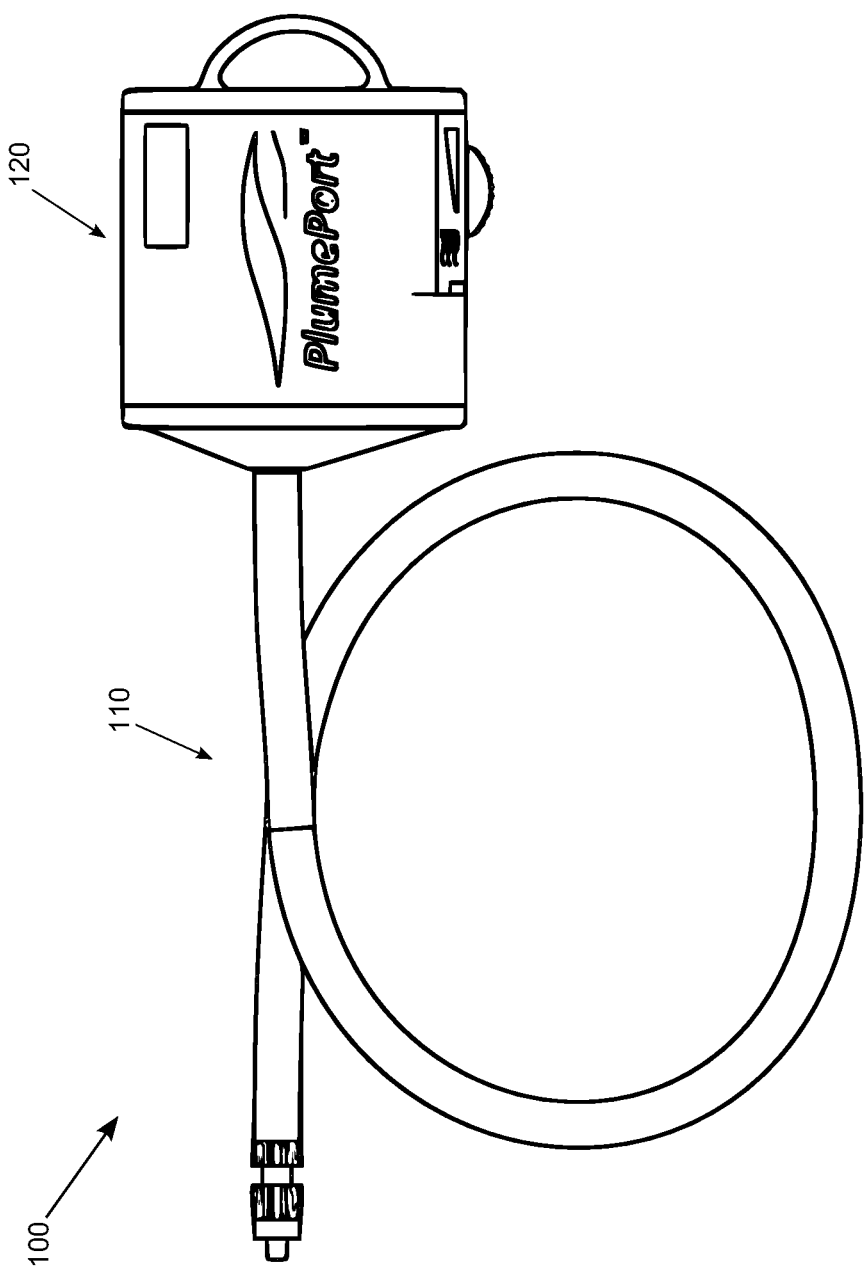
FIG. 1 is a side view of a first embodiment fluid filter system.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

Referring now to the drawings, FIG. 1 discloses a first embodiment 100 of a device and/or system for filtering a fluid. Fluid filter system 100 comprises an input hose portion 110 and filter housing (or filter capsule or cartridge) 120.

Figure 2:
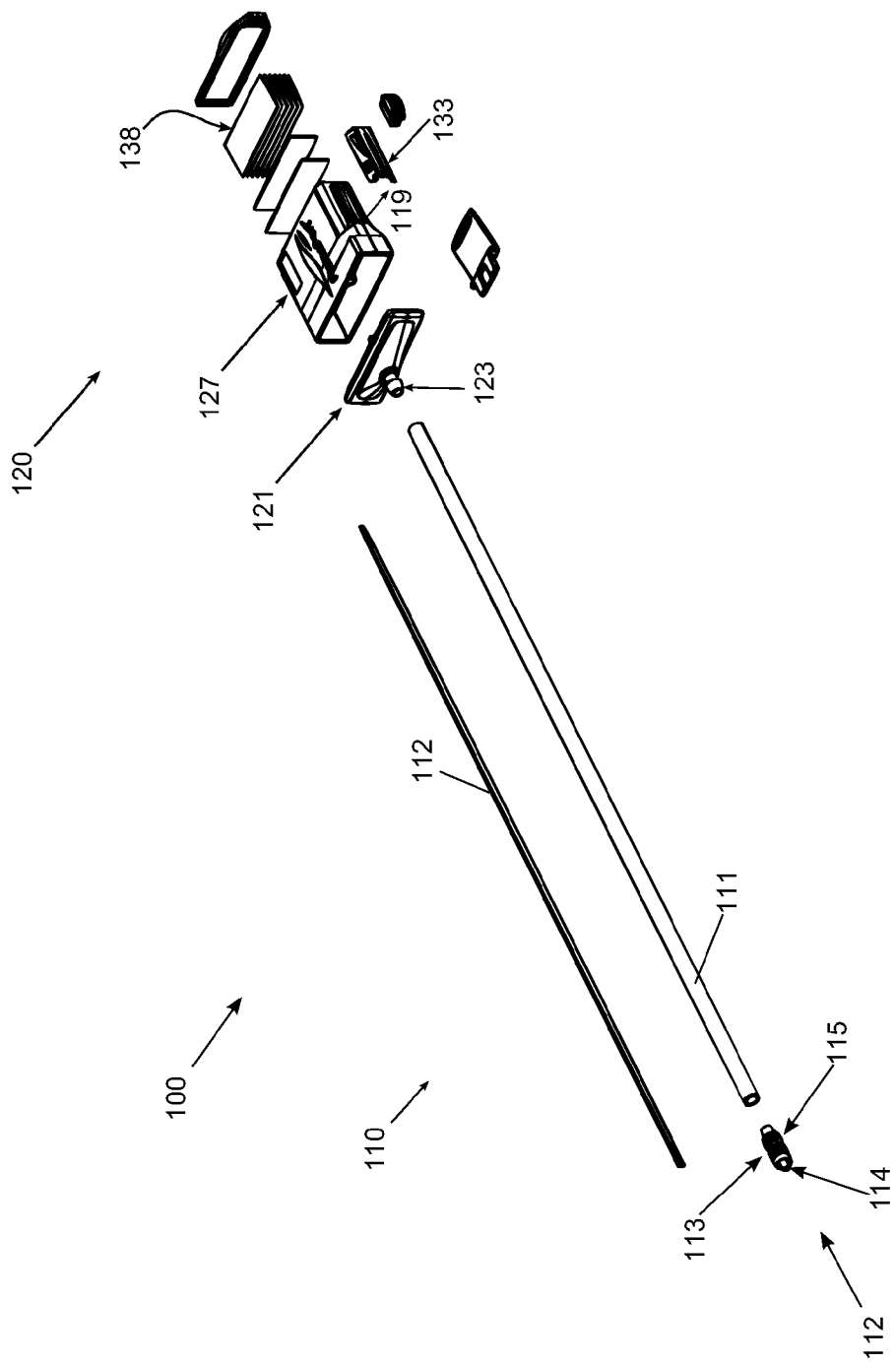
FIG. 2 is an exploded isometric view of the fluid filter system shown in FIG. 1.

As shown in FIG. 2, input hose portion 110 contains input adapter 113, flexible tube 111, and wick 112. Input adapter 113 has input side 114 and opposite output side 115. Input side 114 acts as a system inlet for attachment to a fluid source for inwards fluid flow 117. In this embodiment, adapter input side 114 is a Luer-Lock adapter, but other similar alternative adapters may be used. Adapter output side 115 is connected to a first input side end of tube 111 through compressive engagement. In this embodiment, tube 111 is a clear flexible tube. Within tube 111 is arranged wick 112. In one embodiment, wick 112 is made of a moisture absorbent or adsorbent material such as PVA.

As shown in FIG. 2, tube 111 has an output side end which compressively engages filter cartridge inlet portion 121 at external inlet 123. External inlet 123 contains friction ridges which help prevent tube 111 from disconnection and also helps to make an air tight seal.

Figure 3:
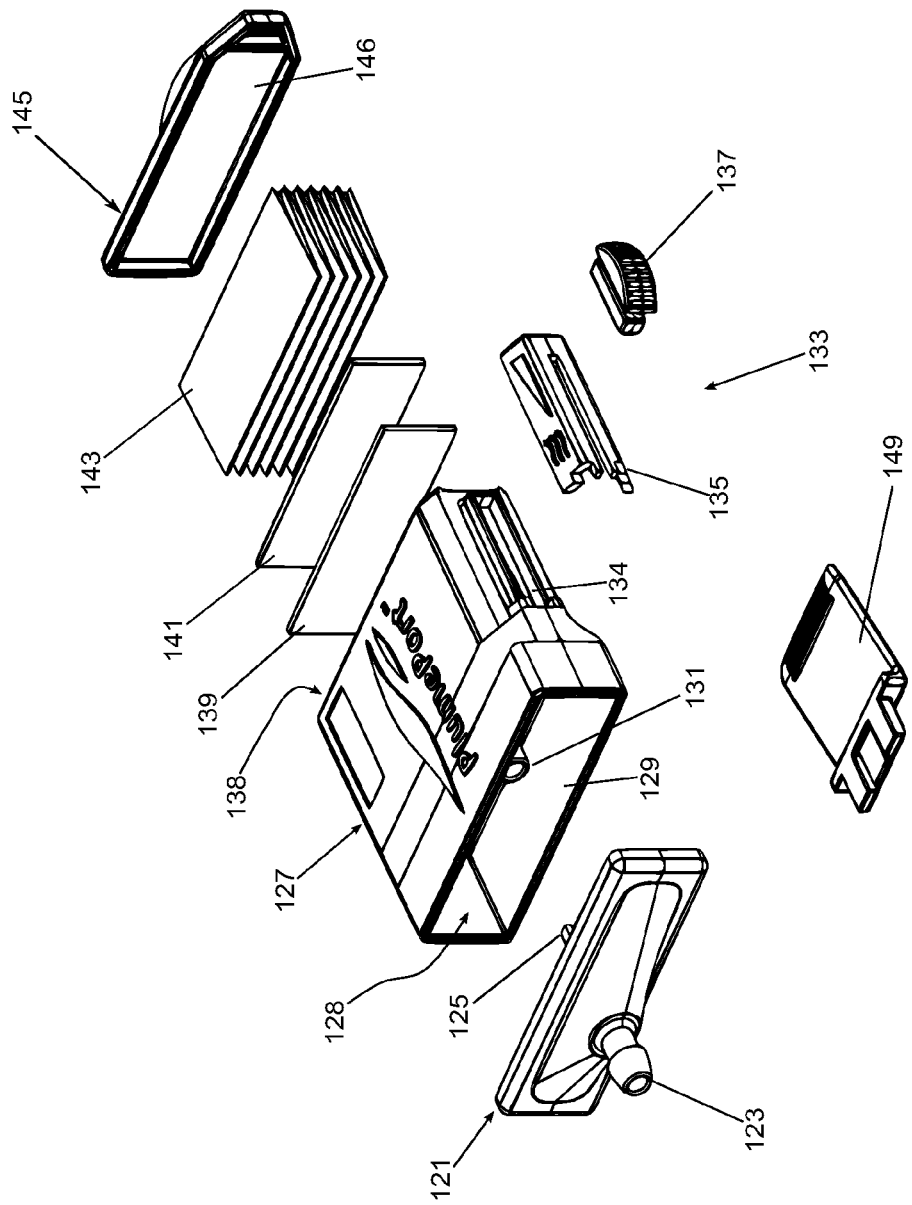
FIG. 3 is a close up exploded partial view of the fluid filter system shown in FIG. 1.

FIG. 3 is a close up exploded isometric view of filter cartridge 120. Filter cartridge 120 contains three housing portions: inlet side portion 121, body portion 127, and end portion 145. Tubular external inlet 123 passes through housing inlet side portion 121 and connects to tubular inlet inner portion 125. Housing inlet portion 121 is ultrasonically welded to housing body portion 127 to form liquid trap chamber 128. Liquid trap chamber 128 has inner surface 129 which acts as an outer boundary for any captured within liquid trap 128. Liquid trap outlet internal side 131 is supported by housing body portion 127. Liquid trap inlet internal side 125 and liquid trap outlet internal side 131 protrude into a generally central region of liquid trap chamber 128. Liquid trap outlet 131 forms a conduit between liquid trap 128 and filter chamber 138.

Filter chamber 138 is formed between housing body portion 127 and housing end portion 145. Housing end portion 145 is ultrasonically welded to housing body portion 127. Arranged within filter chamber 138 of one embodiment are first filter media 139, second filter media 141, and third filter media 143. First filter media 139 is hydrophobic fibrous filter media. Second filter media 141 is activated charcoal media. Third filter media is a pleated fibrous filter media. Other embodiments may include one or two of the foregoing media and/or other similar media.

Housing body portion 127 connects to valve slide retainer 135. On the outer surface of housing body portion 127 facing valve slide retainer 135 is valve passage 134. Valve slide 137 is arranged to selectively block passage 134 as will be discussed in greater detail below. Also shown in FIG. 3 is attachment clip portion 149.

Figure 4:
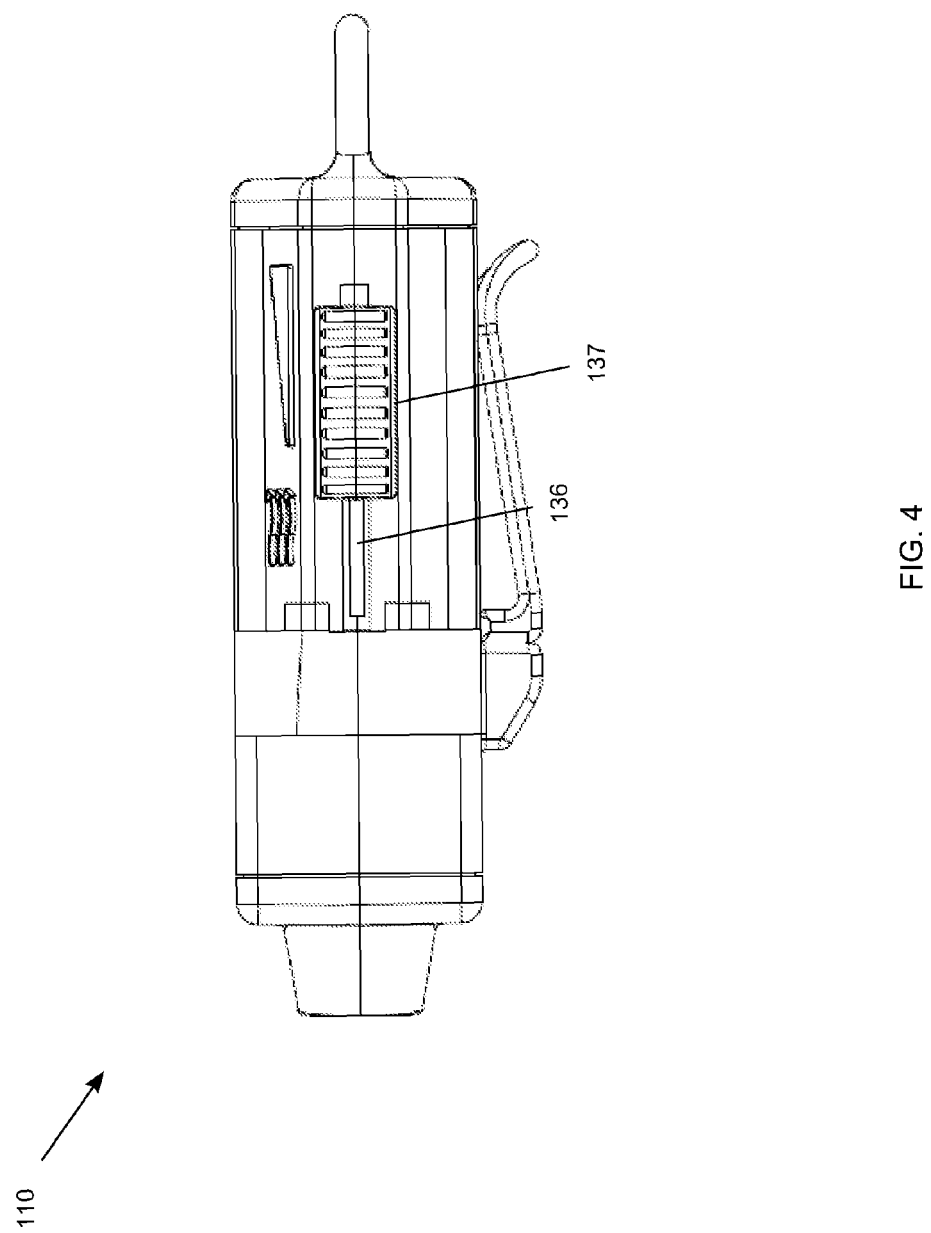
FIG. 4 is a bottom view of the fluid filter system shown in FIG. 1.

FIG. 4 is a bottom view of filter cartridge 120 showing opening 136 and valve slide 137.

Figure 5:
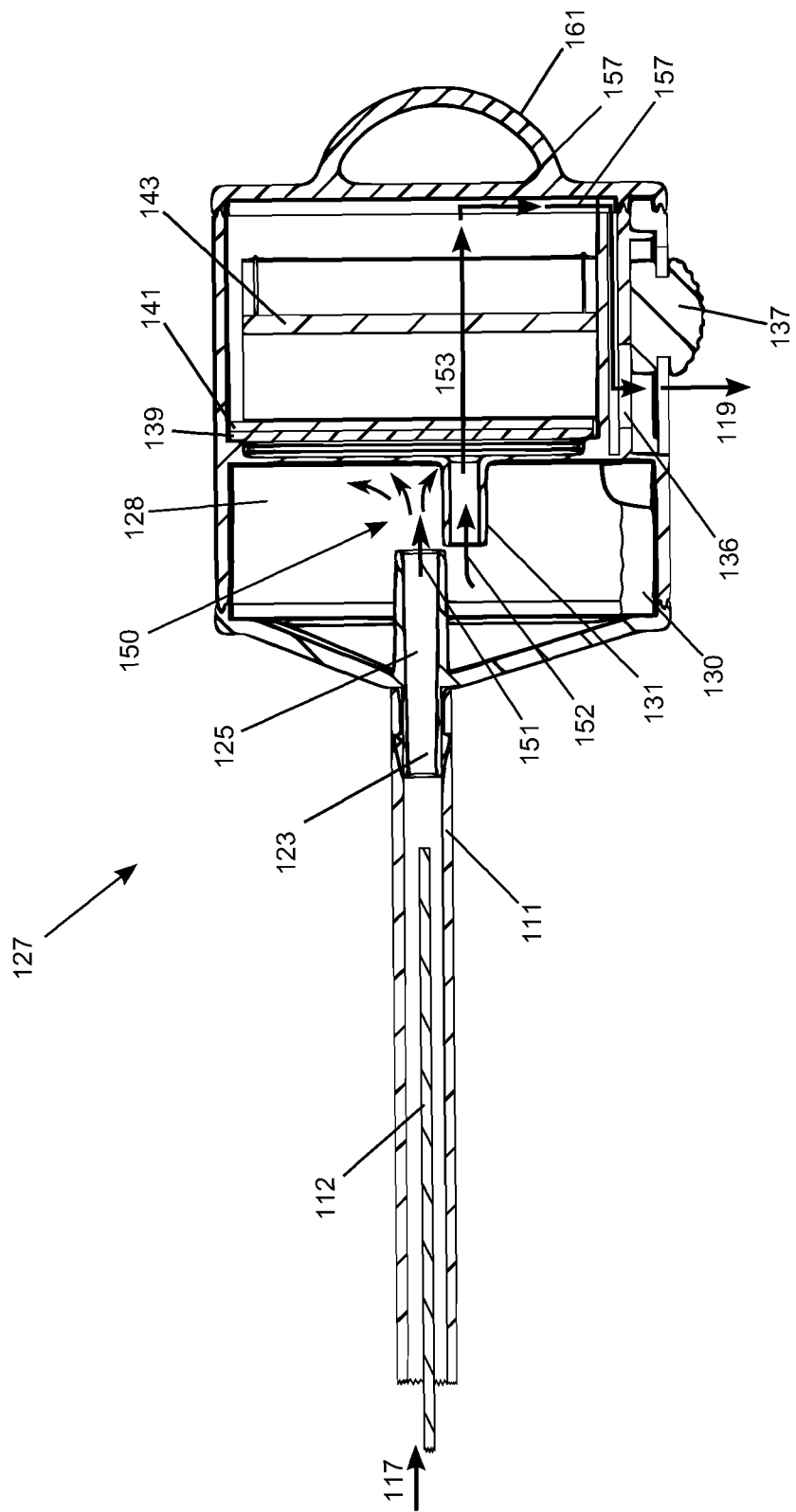
FIG. 5 is a section view of the fluid filter system taken along line 5-5 in FIG. 4.

FIG. 5 is vertical section of filter system 120 showing the flow of fluid from first into filter system 117 through the filter system and out of the system 119. As shown in FIG. 5, tube 111 has a larger diameter than wick 112. This allows fluid to flow inwards 117 through tube 111. Moisture that is in fluid passing past wick 112 may be absorbed or adsorbed by wick 112. Fluid flow continues rightwards and passes from tube 111 through liquid trap inlet outer side 123. Flow continues rightwards through fluid trap inlet inner side 125 and out 151 of inlet inner side 125 into liquid trap chamber 128. Straight inertial flow of fluid out of liquid trap 125 does not flow directly into filter trap outlet 131. Rather, fluid flow is forced to circulate within chamber 128 before passing out of chamber 128. Liquid within the flow 151 falls within chamber 128 and pools at a lower region 120 of liquid trap 130. Liquid trap inlet 125 and liquid trap outlet 131 are arranged in the central region 150 of liquid trap chamber 128. After fluid circulates within chamber 128, pressure causes it to pass out liquid trap outlet 131. Fluid flow continues rightwards 153 out of outlet 131 into filter chamber 138. Flow within filter chamber 138 first must pass through first filter media 139. Since filter media 139 is hydrophobic, any liquid remaining in the flow may be prevented from passing further rightwards.

In one embodiment, flow next passes through filter media 141, which absorbs/adsorbs/deactivates odors, an/or chemical contained within the flow. Flow next passes through filter media 143. The pleats of filter media 143 create a large surface area which allows the use of ULPA media, for example, with very small pores while keeping flow resistance lower than a similar unpleated media. Flow continues rightwards towards the right boundary of housing end portion and passes into passageway 157. Passageway 157 directs flow towards valve 133. More specifically, flow continues through passageway 157 out through opening 136 in housing body portion and out of the filter system 119. The horizontal position of valve slide 137 affects the flow rate by selectively blocking opening 136. When slide 137 is pushed fully leftwards, opening 136 will be completely blocked fully stopping fluid flow through system 100. When slide 137 is pushed fully rightwards, opening 136 is not obstructed by valve 137 at all and flow is not obstructed by valve 133.

FIGS. 6-9 demonstrate how the liquid trap will work in any orientation. Fluid will collect at a lower region 130 within the fluid trap. Because liquid trap inlet 125 and liquid trap outlet 131 are centrally located 150 within liquid trap chamber 128, lower liquid region 130 will always be separated from the outlet and inlet.

Figure 10:
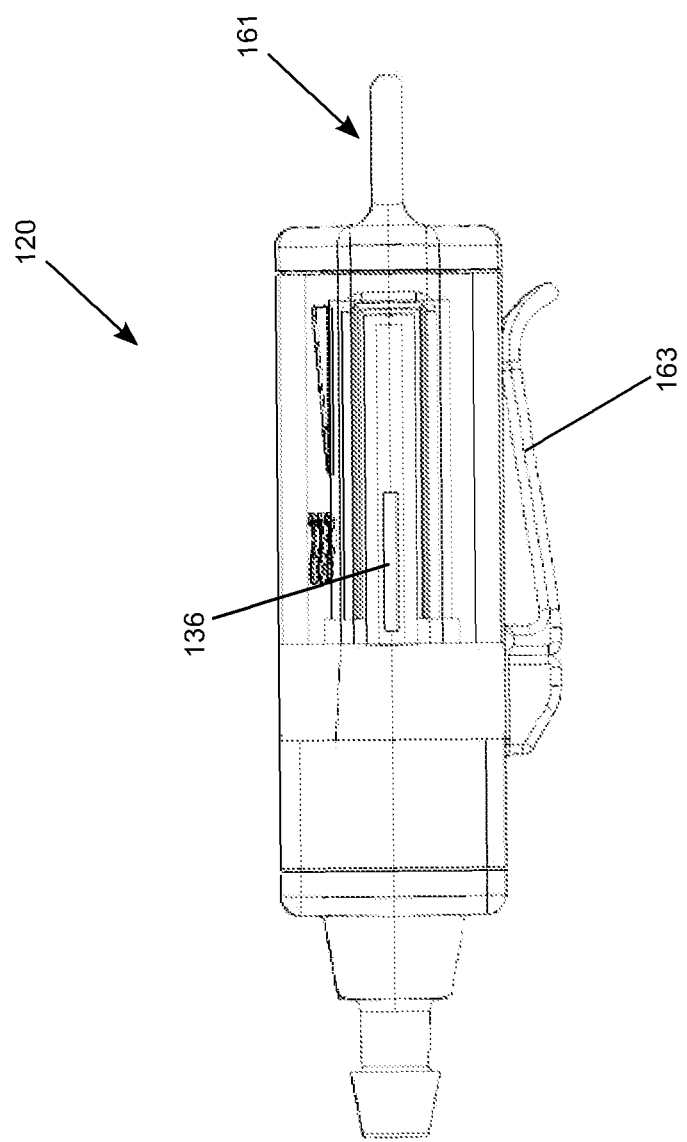
FIG. 10 is a partial bottom view of the fluid filter system shown in FIG. 1 with the valve slide removed.
Figure 11:
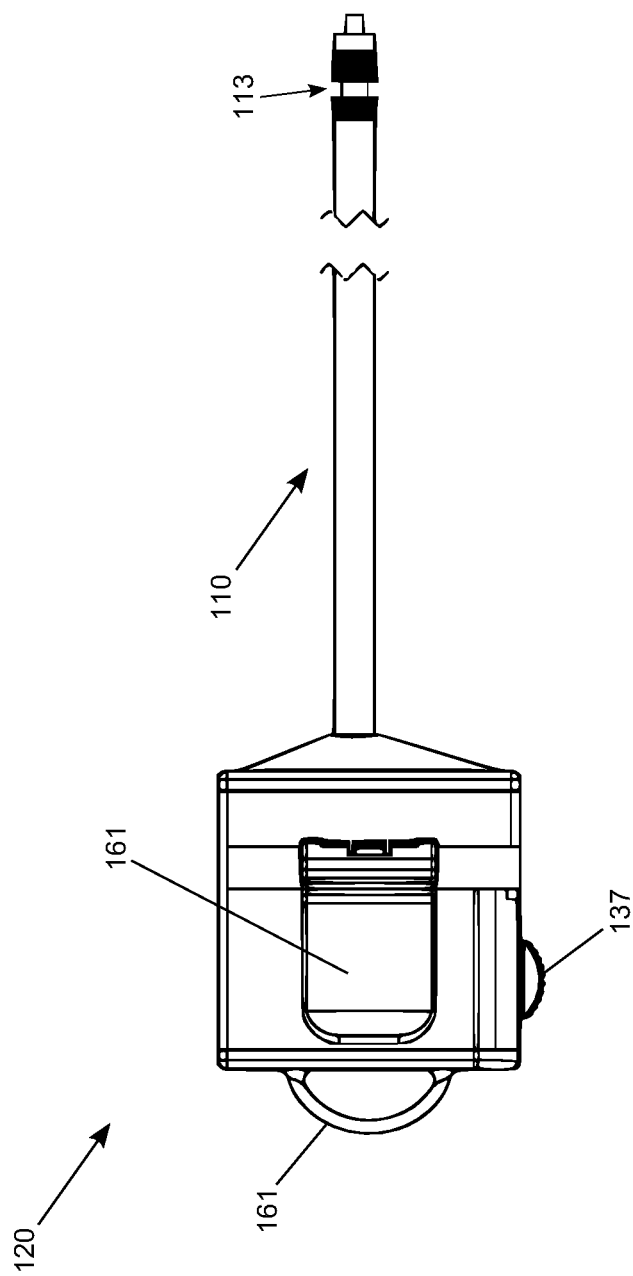
FIG. 11 is a rear view of the fluid filter system shown in FIG. 1.

FIGS. 10 and 11 show attachment loop 161 and attachment clip 163. Attachment loop 161 is useful for attachment to an IV pole or other similar object. Attachment clip 163 is useful for attachment to a drape.

Figure 13:
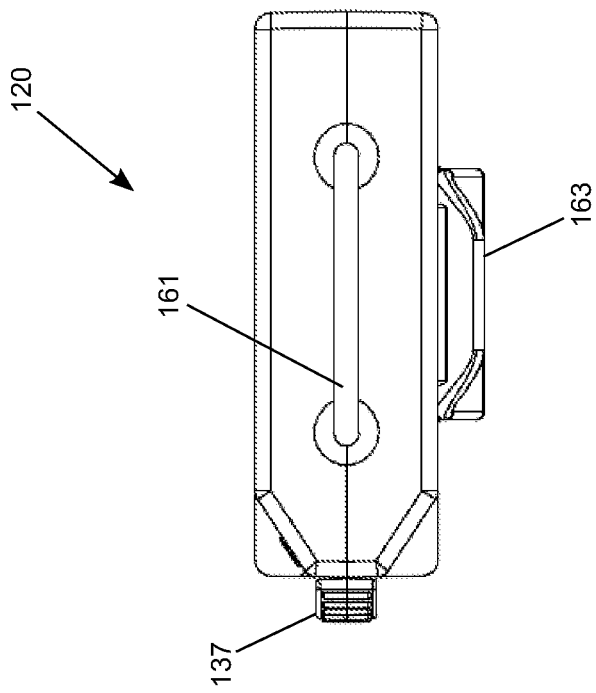
FIG. 13 is a right side view of the fluid filter system shown in FIG. 1.
Figure 12:
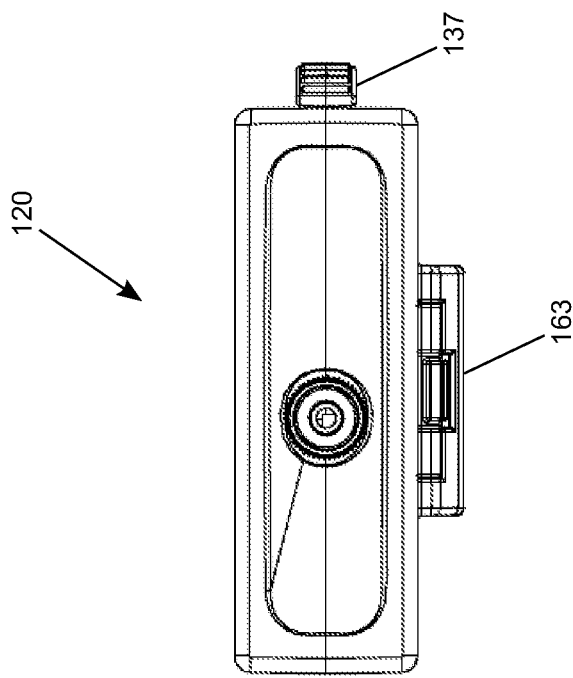
FIG. 12 is a left side view of the fluid filter system shown in FIG. 1.

FIGS. 12 and 13 illustrate the left side view and the right side view of fluid filter cartridge 120.

Figure 14:
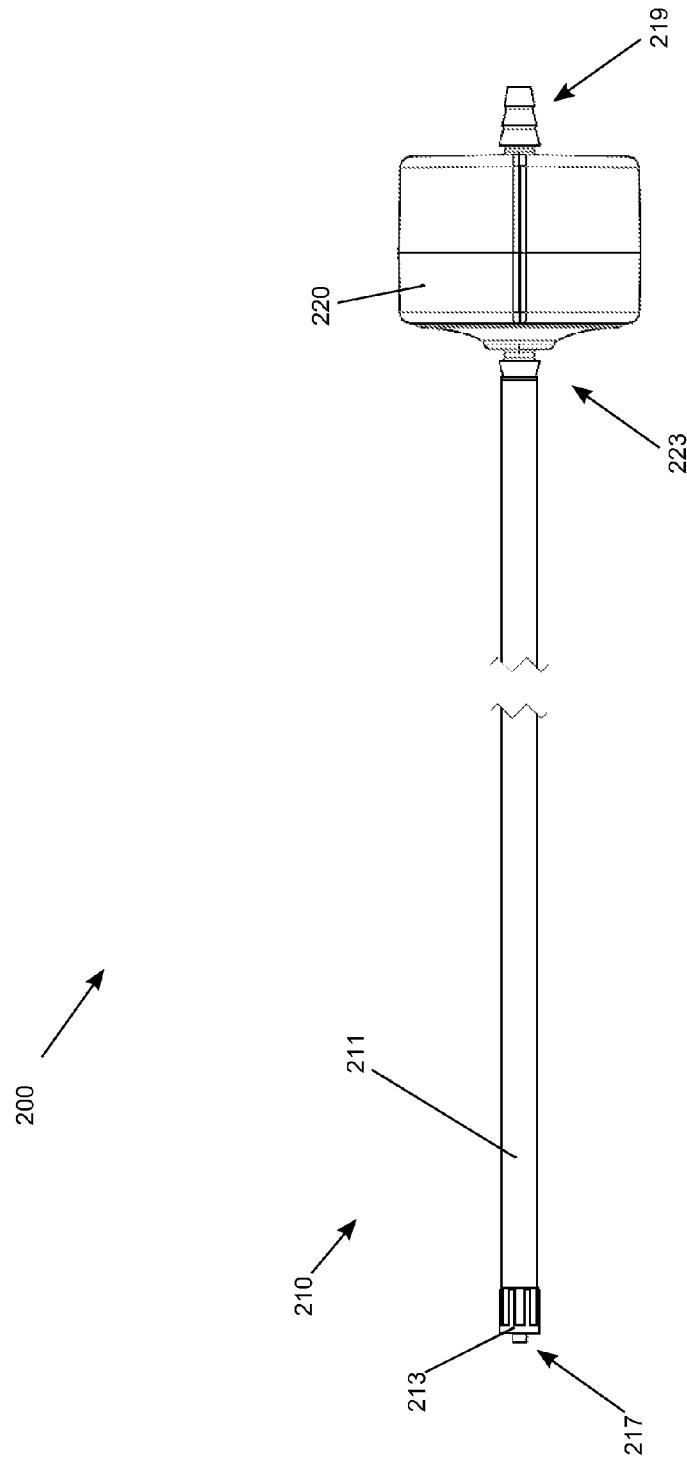
FIG. 14 is a side partial view of a second embodiment fluid filter system.
Figure 15:
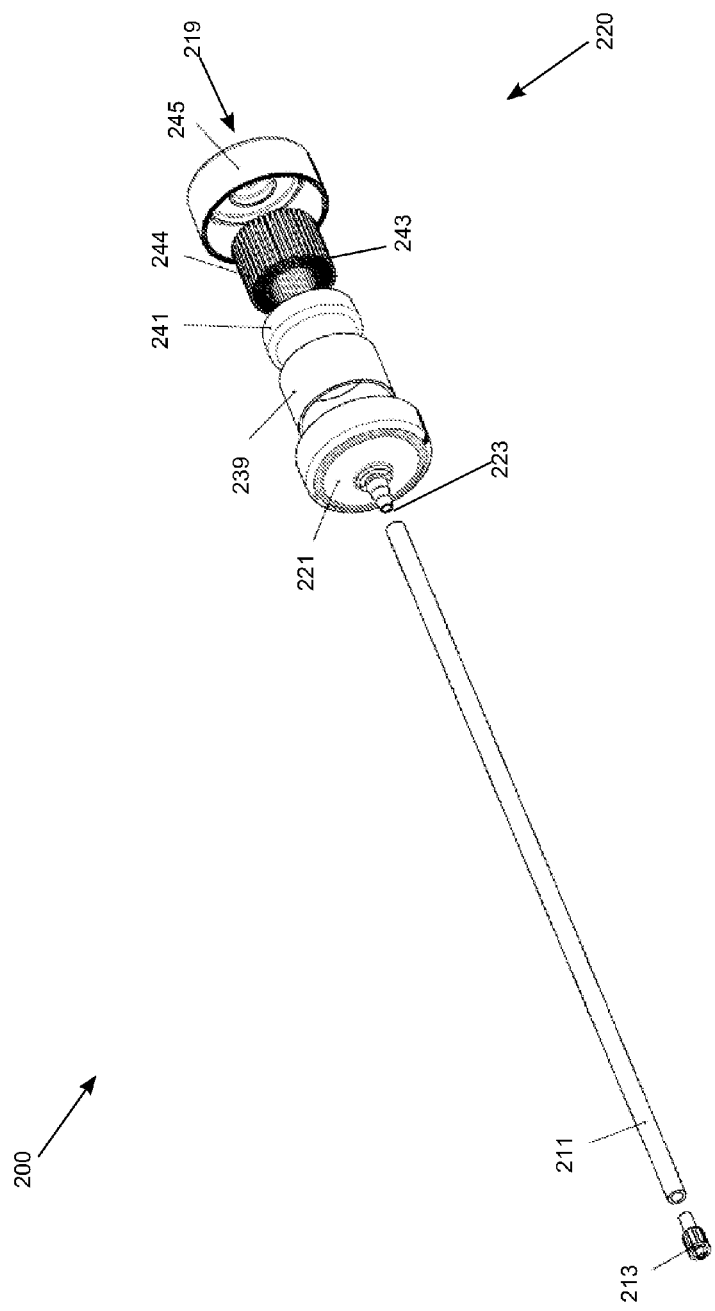
FIG. 15 is an exploded isometric view of the filter system shown in FIG. 14.

FIG. 14 shows second embodiment filter system 200. Filter system 200 has flexible input tube portion 210, filter cartridge portion 220, system inlet 217, and system outlet 219. As shown in the exploded isometric view of FIG. 15, system 200 has input adapter 213, compressively connected to tube 211, which compressively connects to inlet outer side 223. Inlet outer side 223 is held by housing inlet portion 221. Within filter cartridge 220 are filter first media 239, filter cap 241, second filter media first layer 243, and second filter media second layer 244. Filter cartridge inlet portion 221 is ultrasonically welded to filter cartridge outlet portion 245.

In this embodiment, first filter media 239 is a cylindrical sleeve of activated carbon media. Second filter media first layer 243 and second layer 244 form a pleated ULPA media. Media cap 241 is arranged adjacent first and second media and blocks direct flow from inlet 223 to outlet 219. The volume generally between cartridge inlet portion 221 and end portion 245 inner walls and the outer cylindrical surface of filter media 239 creates a liquid trap. More specifically, since the outer cylindrical diameter of the filter media is less than the inner diameter of the cartridge housing, liquid will fall into the region below the filter media. In order to pass out of the filter cartridge housing, liquid would need to go up against gravity through the filter media to flow out 219.

Figure 16:
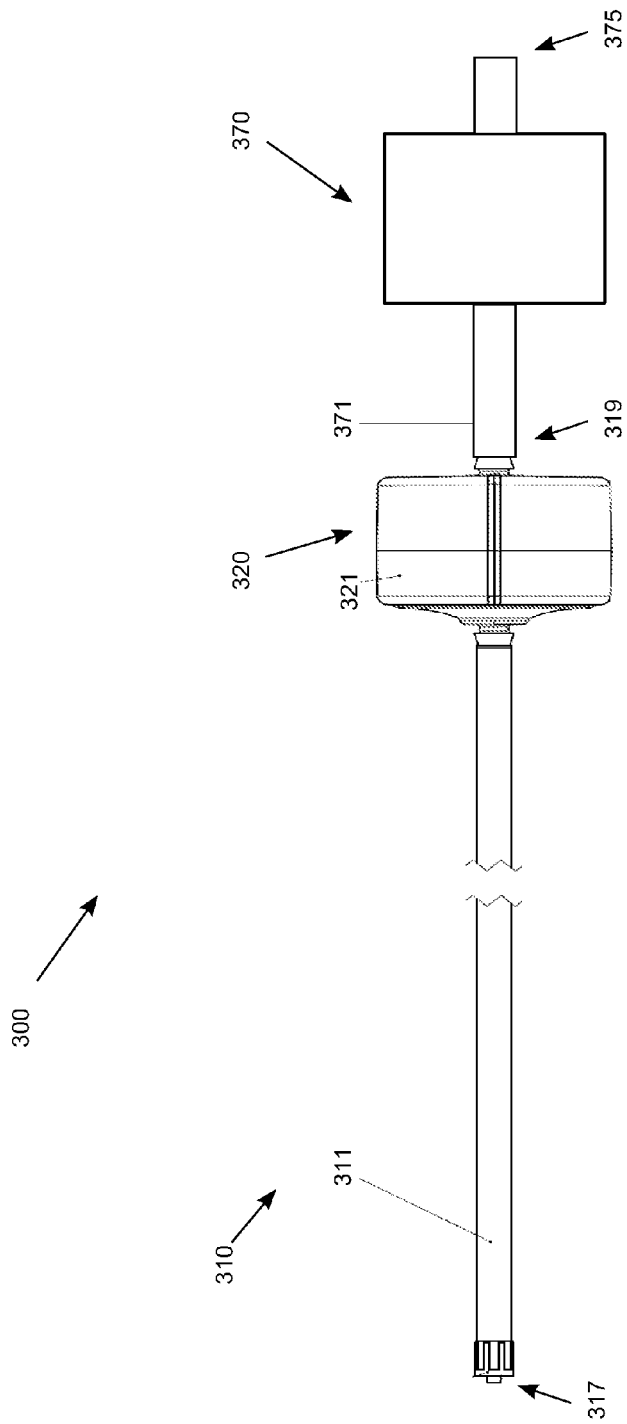
FIG. 16 is a side view of a third embodiment filter system.

Shown in FIG. 16 is third embodiment filter system 300. System 300 is similar to systems 100 and 200 and also contains suction unit 370 configured and arranged to provide vacuum suction. System 300 generally includes inlet 317, input tube portion 310, filter cartridge 320, and suction unit 370. Input tube portion 310 is similar in the first and second embodiments. Suction unit 370 is an blower, a pump, or impellor such as a Multicomp USA, Part # MC32897 impellor. Suction 370 is configured to provide suction to aid the flow of fluid from inlet 317 out through outlet 375. System 300 can be used in a laparoscopic surgical setting in which inlet 317 is connected to a pressurized surgical site, and 375 is fed into ambient air. However, blower 370 can be configured such that it provides the substantial portion of the fluid flow drive through system 300. System 300 can also be configured such that it does not use any portion of the pressure differential between the surgical site and ambient air for causing fluid flow.

In addition, each of the disclosed filter system embodiments may modified to also contain an RF transponder for communication with a trocar, a insufflator, or smartboom. The disclosed embodiments may further contain one or more one way valves and the valves may be placed at the liquid trap chamber inlet and/or outlet, the filter chamber inlet and/or outlet, and/or the filter system inlet and/or outlet. The valves may also be automatic valves or electronic valves. The valves may also be biased to be normally closed to prevent any fluid in the filter system from exiting the system when the flow drive is off.

The described embodiments provide a number of unexpected results and advantages over the prior art. For example, filter media life may be prolonged by preventing moisture and fluid from in the fluid flow from reaching the filter media. In another aspect, if during laparoscopic surgery blood or other body fluids is passed out of the trocar, it may be intercepted by the wick or the liquid trap before reaching and damaging the filter media. Additionally, the variable valve in certain embodiments allows the filter system to be used in a variety of operating conditions, flow rates, and pressure differentials. Further the clip and clamp provide significant usability improvements by allowing the device to be easily mounted, reducing the strain on the very sensitively held trocar. The filter system has a small form factor, made possible through the combined use in certain embodiments of filter media pleating and filter media lifetime enhancement from the moisture capture techniques. Finally, the efficient combination of elements of the filter system produces a highly economical device that is appropriate for disposable use.

Therefore, while the presently-preferred form of the method and device for a filter system has been shown and described, and several modifications discussed, persons skilled in this art will readily appreciate that various additional changes may be made without departing from the scope of the invention.

The invention claimed is:

1. A medical fluid filter system comprising:
a housing comprising:
  a liquid trap chamber having a volume;
  a filter media chamber;
  a filter media arranged within said filter media chamber;
  said liquid trap chamber having a liquid trap outlet port providing a fluid passageway between said liquid trap chamber and said filter media chamber;
  said liquid trap outlet port configured and arranged within said liquid trap chamber to inhibit flow of liquid from said liquid trap chamber to said filter media chamber and configured and arranged to allow gas to flow from said liquid trap chamber to said filter media chamber;
a filter system inlet passing through said housing for intake of fluid originating from a surgical site; and
a filter system outlet passing through said housing for fluid exhaust.

2. The medical fluid filter system as set forth in claim 1, wherein said liquid trap outlet port is generally near the center of volume of said liquid trap chamber.

3. The medical fluid filter system set forth in claim 1, wherein said liquid trap outlet port is above a lowest position within said liquid trap chamber for any orientation of said system in a gravitational field.

4. The medical fluid filter system set forth in claim 1, wherein said liquid trap outlet port is arranged in a position separated from an inner surface of said liquid trap chamber towards a generally central region of said liquid trap chamber.

5. The medical fluid filter system set forth in claim 1, wherein said liquid trap chamber has an inlet port in fluid communication with said system inlet and configured and arranged within said liquid trap chamber to inhibit flow of liquid from said liquid trap chamber out of said inlet port.

6. The medical fluid filter system as set forth in claim 2, wherein said liquid trap chamber has an inlet port in fluid communication with said system inlet and configured and arranged within said liquid trap chamber to inhibit flow of liquid from said liquid trap chamber out of said inlet port and said fluid trap inlet port is generally near the center of volume of said liquid trap chamber.

7. The medical fluid filter system set forth in claim 1, and further comprising a filter media configured and arranged to filter surgical smoke.

8. The medical fluid filter system set forth in claim 1, and further comprising a sliding valve.

9. The medical fluid filter system set forth in claim 1, and further comprising a blower.

10. The medical fluid filter system set forth in claim 1, and further comprising a liquid exit port.

11. A medical fluid filter system comprising:
a filter system inlet for intake of fluid originating from a surgical site;
a housing in fluid communication with said filter system inlet, said housing comprising:
a filter media chamber for receiving a filter media;
a liquid trap chamber for retaining liquids from said fluid and said liquid trap chamber having a volume;
a generally tubular liquid trap outlet extending into said volume and providing a fluid passageway between said liquid trap chamber and said filter media chamber; and
a filter system outlet passing through said housing for fluid exhaust.

12. The medical fluid filter system set forth in claim 11, wherein said liquid trap outlet has an end located generally near the center of volume of said liquid trap chamber.

13. The medical fluid filter system set forth in claim 11, wherein said liquid trap outlet port and said fluid trap inlet port share a common wall.

14. The medical fluid filter system set forth in claim 11, wherein said liquid trap chamber and said filter media chamber share a common wall.

15. The medical fluid filter system set forth in claim 11, and further comprising a filter media configured and arranged to filter surgical smoke.

16. The medical fluid filter system set forth in claim 15, and further comprising a moisture indicator for indicating when said filter media is wet.

17. The medical fluid filter system set forth in claim 11, wherein said liquid trap chamber contains an inner peripheral surface for containing a liquid in at least two orientations of said medical fluid filter system.

18. The medical fluid filter system set forth in claim 11, and further comprising a sliding valve.

19. The medical fluid filter system set forth in claim 11, and further comprising a blower.

20. The medical fluid filter system set forth in claim 11, wherein said system is configured and arranged to use an inertial force caused by a circular flow path to separate liquid from said fluid.

* * * * *